(12) United States Patent
Seligman

(10) Patent No.: US 7,869,883 B2
(45) Date of Patent: Jan. 11, 2011

(54) GENERAL PURPOSE ACCESSORY FOR A COCHLEAR IMPLANT SYSTEM

(75) Inventor: Peter Seligman, Essendon (AU)

(73) Assignee: Cochlear Limited, Lane Cove (AU)

( * ) Notice: Subject to any disclaimer, the term of this patent is extended or adjusted under 35 U.S.C. 154(b) by 1009 days.

(21) Appl. No.: 11/645,756

(22) Filed: Dec. 27, 2006

(65) Prior Publication Data

US 2007/0106345 A1 May 10, 2007

Related U.S. Application Data

(63) Continuation of application No. 10/466,149, filed as application No. PCT/AU02/00036 on Jan. 14, 2002, now Pat. No. 7,174,214.

(30) Foreign Application Priority Data

Jan. 12, 2001 (AU) .................................... PR2504

(51) Int. Cl.
*A61N 1/00* (2006.01)
(52) U.S. Cl. ....................................................... 607/57
(58) Field of Classification Search ............. 607/55–57, 607/137; 623/10; 600/25
See application file for complete search history.

(56) References Cited

U.S. PATENT DOCUMENTS

| | | | |
|---|---|---|---|
| 4,741,339 A | 5/1988 | Harrison et al. | |
| 5,597,380 A | 1/1997 | McDermott et al. | |
| 5,824,022 A | 10/1998 | Zilberman et al. | |
| 5,935,166 A | 8/1999 | Kennedy | |
| 6,010,532 A * | 1/2000 | Kroll et al. ..................... 623/10 |
| 6,141,588 A | 10/2000 | Cox et al. | |
| 6,272,382 B1 | 8/2001 | Faltys et al. | |
| 6,491,722 B1 | 12/2002 | Kroll et al. | |
| 6,748,094 B1 | 6/2004 | Tziviskos et al. | |
| 6,766,201 B2 | 7/2004 | Von Arx et al. | |
| 6,924,773 B1 | 8/2005 | Paratte | |
| 7,020,298 B1 | 3/2006 | Tziviskos et al. | |
| 7,174,214 B2 | 2/2007 | Seligman | |
| 2002/0071581 A1 | 6/2002 | Leysieffer et al. | |
| 2004/0088051 A1 | 5/2004 | Seligman | |
| 2005/0192648 A1 | 9/2005 | Killian et al. | |
| 2008/0300658 A1 | 12/2008 | Meskens | |

FOREIGN PATENT DOCUMENTS

WO 02/056637 7/2002

OTHER PUBLICATIONS

International Search Report of PCT/AU02/00036, dated Feb. 18, 2002.
International Preliminary Examination Report of PCT/AU02/00036 dated Oct. 10, 2002.

* cited by examiner

*Primary Examiner*—George Manuel
(74) *Attorney, Agent, or Firm*—Kilpatrick Stockton LLP

(57) ABSTRACT

A cochlear implant system comprising a first unit adapted to be worn on or in one ear of an implantee. The first unit has a case housing componentry including a microphone, and a speech processor means. A second unit or accessory is adapted to be worn on or in the other ear of the implantee. The second unit or accessory has a case housing a second power source. An electrical conduction means for transmitting power from the second power source to the componentry of the first unit extends between the first and second units. Such a conduction means can extend around the back of the head of the implantee.

22 Claims, 3 Drawing Sheets

GENERAL PURPOSE ACCESSORY FOR A COCHLEAR IMPLANT SYSTEM

CROSS-REFERENCE TO RELATED APPLICATIONS

This application is a continuation of U.S. patent application Ser. No. 10/466,149 filed on Dec. 10, 2003, entitled, "General Purpose Accessory for a Cochlear Implant System" which is a national stage application of PCT/AU2002/000036, entitled "General Purpose Accessory for a Cochlear Implant System" and filed on Jan. 14, 2002, and which claims priority from Australian Patent Application PR 2504, entitled "General Purpose Accessory for a Cochlear Implant System" which was filed on Jan. 12, 2001.

FIELD OF THE INVENTION

The present invention relates to an accessory for use with a cochlear implant system.

BACKGROUND OF THE INVENTION

In many people who are profoundly deaf, the reason for deafness is absence of, or destruction of, the hair cells in the cochlea which transduce acoustic data signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the implanted. This transcutaneous transmission occurs via the external transmitter coil which is positioned to communicate with an implanted receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

Traditionally, the external componentry has been carried on the body of the implantee, such as in a pocket of the implantee's clothing, a belt pouch or in a harness, while the microphone has been mounted on a clip mounted behind the ear or on the lapel of the implantee.

More recently, due in the main to improvements in technology, the physical dimensions of the speech processor have been able to be reduced allowing for the external componentry to be housed in a small unit capable of being worn behind the ear of the implantee. This unit allows the microphone, power unit and the speech processor to be housed in a single unit capable of being more discretely worn behind the ear, with the external transmitter coil still positioned on the side of the implantee's head to allow for the transmission of the coded sound signal from the speech processor and power to the implanted stimulator unit. The availability of such behind-the-ear (BTE) units has provided a great benefit to cochlear implant system recipients and provided them with a new found freedom. This has been due in the main to there no longer being a need to carry a large unit around with them and the associated long cables to connect the body worn device to the microphone and the transmitter coil positioned on the side of their head.

While the dimensions of behind-the-ear units have reduced significantly from those worn on the body, the units are typically still larger than most conventional hearing aids due in the main to the space requirements for the speech processor and batteries within this unit as well as the intrinsic differences between hearing aids and cochlear implant devices. As behind-the-ear units need to satisfy the power requirements of the implant, a large proportion of the size of conventional behind-the-ear devices has been associated with housing the power source (batteries) to provide such power requirements. As the power requirements of implant recipients vary depending upon the coding strategies that are employed and the skin flap thickness of the recipient across which the power needs to be transmitted, a main design limitation of conventional behind-the-ear devices has resided in housing a sufficient power supply to cater for all recipient types.

While continuing improvements in microprocessor and battery design should lead to further miniaturisation of behind-the-ear units, perhaps to the extent that the unit could be worn within the ear, implantee expectations as to the level of performance and features of cochlear implant are also expected to increase. In order to meet this implantee-expectation, it is anticipated that there would need to be an unacceptably large increase in the size of presently known behind the ear units so negating any efforts to further miniaturise such units in the future.

Further to this, in most cases of cochlear implantation, the implant has only been implanted in one of the patient's cochleas, with the decision upon which ear the implantation is to occur being the result of extensive pre-operative consideration. Due to the design requirements of the conventional system, the cochlear implant system user finds that if they desire to wear a behind-the-ear processor, then in most cases they will wear it on the ear that has been implanted in order to reduce the amount of connecting leads required. It has been accepted that in the majority of cases when the patient has been implanted in only one ear, that for simplicity of use, the behind-the-ear unit has been won on the ear which has been implanted and only in special circumstances would this practice be altered.

The present invention therefore aims to provide a cochlear implant system which is capable of allowing more functionality to be incorporated in behind-the-ear units without increasing the sizes of such units and compromising the benefits which such systems provide to implant recipients.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element integer or step, or group of elements, integers or steps.

As described, it is considered that with the increasing popularity of behind-the-ear units or even take up of in-the-ear units, cochlear implant system recipients will expect such devices to provide features additional to those considered as standard at present. The present invention is directed to meeting this expectation while ensuing that the unit remain at an acceptably small size. The additional features envisaged as being required as standard include: a built in telecoil for picking up signals from a telephone; the ability to detect sounds from both sides of the head rather than just the side of the head that the BTE unit is positioned on; sufficient power resources to use all speech processing strategies; adequate battery life to enable the device to operate for a significant time without the need to recharge or replace the batteries; and a radio receiver and the like for classroom or other remote signal source use.

According to one aspect, the present application is directed to a first invention comprising a cochlear implant system comprising:

a first unit adapted to be worn on or in one ear of an implantee, the first unit having a case housing componentry including a microphone that detects sounds and outputs acoustic data signals representative of the detected sounds, and a speech processor means that receives the acoustic data signals;

a second unit adapted to be worn on or in the other ear of the implantee, the second unit having a case housing a power source; and a power transmission means for transmitting power from the power source of the second unit to at least some of the componentry of the first unit.

The use of a power source in the second unit can provide a number of advantages. For example, the power source of the second unit can provide the implantee with more power or power for a longer time than is available from the use alone of an on-board power source. Saying this, the first unit can, in one embodiment, have an on-board power source.

The use of the power source in the second unit also potentially allows a reduction in the dimensions of the first unit as a smaller on-board power source can potentially be utilised due to the presence of the additional power source in the second unit.

The speech processor means of the first unit can convert the received acoustic data sign into coded signals that are transmittable through a communication link to an implantable cochlear stimulator. The communication link preferably comprises a radio frequency link created between an external antenna coil and an implantable antenna coil. Other suitable communication links can be envisaged.

In this aspect, the second unit can further house a second microphone that detects sounds and outputs acoustic data signals representative of the detected sounds.

The power transmission means can comprise an electrical conduction means, such as electrically conducting wire or wires.

Still further, the system can comprise a signal transmission means whereby the acoustic data signals output by the second microphone are transmittable to the speech processor means of the first unit.

Where both are present, the signal transmission means and power transmission means can be housed in a common cable extending between the first unit and the second unit. It will, however, be appreciated that the respective signal transmission and power transmission means could comprise separate cables. Such one or more cables are preferably removably connectable with the first unit and/or the second unit. The one or more cables are preferably sufficiently long to just reach between the first and second unit, when such units are mounted on or in the respective ears of the implantee. In one embodiment the one or more cables can be extendible or adjustable in length.

In another embodiment, the signal transmission mans can comprise a wireless means, such as a short-distance radio frequency (RF) link.

In a further embodiment, the respective cases of the first unit and second unit can each have an ear hook extending therefrom to allow the cases to be worn behind the respective ears of the implantee. Instead, either or both of the first and second units can have a case adapted to be worn or fit with the ear canals of the implantee. In one embodiment, the case of the first unit is adapted to fit into one ear canal and the case of the second unit is adapted to fit into the ear canal of the other ear.

The second unit of the system can further house a receiver unit that detects signals from an external source and outputs acoustic data signals representative of the detected signals to the speech processor using the signal transmission means. The receiver unit can be selected from the group comprising a telecoil and a radio receiver.

In a further embodiment, the power source of the second unit can comprise one or more batteries. These batteries can be rechargeable.

In a preferred embodiment of this aspects the power source of the second unit also provides power to at least some and preferably all of the componentry of the second unit in another embodiment, the power source of the second unit can be used to provide power to all of the components of the first unit.

In a still further embodiment the second unit has a switch means that, when operated can activate and deactivate componentry of the second unit.

In another embodiment, the second unit can house a second microphone that detects sounds and outputs acoustic data signals representative of the detected sounds, and a second speech processor means that receives the acoustic data signals and converts the signals into coded signals representative of the detected sounds, with the system further comprising a signal transmission means whereby the coded signals output by the second speech processor means are transmittable to the first unit.

In this embodiment, the second speech processor means can use a different speech processing strategy to that of the speech processor means housed in the first unit. In another embodiment the second speech processor means can use the same speech processing strategy to that of the speech processor means housed in the first unit.

In this aspect, the first speech processor means of the first unit can be deactivated when the second speech processor means is in use. Such deactivation can occur automatically on commencement of use of the second unit or can be manually controlled by the implantee.

Where the first unit has an on-board power source, use of the power source of the second unit by the first unit can occur automatically on commencement of use of the second unit. For example, the first unit can be adapted to preferentially, and when available, draw power from the power source of the second unit on electrical connection of the second unit to the first unit. In another embodiment selection of which power source is utilised can be controlled by the implantee, a clinician or another person.

In another aspect the present application is directed to a second invention comprising a cochlear implant system that in turn is comprised of:

a first unit adapted to be worn on or in one ear of an implantee, the first unit having a case housing componentry including a microphone that detects sounds and outputs acoustic data signals representative of the detected sounds, and a first speech processor means that receives the acoustic data signals;

a second unit adapted to be worn on or in the other ear of the implantee, the second unit having a cue housing a power source, a second microphone that detects sounds and outputs acoustic data signals representative of the detected sounds, and a second speech processor means that receives the acoustic data so and converts the signals into coded signals representative of the detected sounds;

a signal transmission means whereby the coded signals output by the second speech processor means are transmitted to the first unit; and a power transmission means for transmitting power from the power source of the second unit to at least some of the componentry of the first unit.

In this aspect, the speech processor means of the first unit converts the received acoustic data signals of the first microphone and/or the coded signals of the second microphone and/or the second speech processor means into signals that are transmittable through a communication link to an implantable cochlear stimulator. In another embodiment, the second speech processor of the second unit can be adapted to convert received acoustic data signals from the second microphone and/or the first microphone and/or the first speech processor means. Transmission of the signals from the first microphone end/or the first speech processor means to the second speech processor means can be by the signal transmission means.

The communication link of this aspect preferably comprises a radio frequency link created between an external antenna coil end an implantable antenna coil. Other suitable communication links can be envisaged.

In this aspect, the speech processor means of the first unit can be deactivated when the second speech processor means is in use. Such deactivation can occur automatically on commencement of use of the second unit or can be manually controlled by the implantee. Still further, the second speech processor means of the second unit can be deactivated when the first speech processor means is in use. Again, such deactivation can occur automatically on commencement of use of the first speech processor means.

In this aspect the power transmission means can comprise an electrical conduction means, such as electrically conducting wire or wires. The signal transmission means and electrical conduction means can also be housed in a common cable extending between the first unit and the second unit. It will however, be appreciated that the respective signal transmission means and electrical conduction means could comprise separate cables. Such one or more cables are preferably removably connectable with the first unit and/or second unit. Again, the one or more cables are preferably sufficiently long to just reach between the first and second unit, when such units are mounted on or in the respective ears of the implantee. In one embodiment, the one or more cables can be extendible or adjustable in length.

In another embodiment of this aspect, the signal transmission means can comprise a wireless means. For example, the wireless means can comprise a relatively short-distance radio frequency (RF) link.

In a further embodiment of this aspect, the respective cases of the first unit and second unit each have an ear hook extending therefrom to allow the cases to be worn behind the respective ears of the implantee. Instead, either or both of the first and second units can have a case adapted to be worn or fit within the ear canals of the implantee. In one embodiment, the case of the first unit is adapted to fit into one ear canal and the case of the second unit is adapted to fit into the ear canal of the other ear.

In a still further embodiment, the second unit further houses a receiver unit that detects signals from an external source and outputs acoustic data signals representative of the detected signals to the second speech processor means within the second unit and/or the first signal processor means housed within the first unit. Where the acoustic data signals are output to the speech processor means within the first unit, the sins are preferably transmittable using the signal transmission means as defined above. The receiver unit can be selected from the group comprising a telecoil and a radio receiver.

In a preferred embodiment of this aspect the power source of the second unit can comprise one or more batteries. Said one or mom batteries can be rechargeable batteries.

In a preferred embodiment of this aspect, the power source of the second unit provides power to at least some and preferably all of the componentry of the second unit. In another embodiment the power source of the second unit can be used to provide power to all of the componentry of the first unit.

In a further embodiment, the first unit can have an-board power source.

In this aspect, where the first unit has an on-board power source, use of the power source of the second unit by the first unit can occur automatically on commencement of use of the second unit. For example, the first unit can be adapted to preferentially, and when available, draw power from the power source of the second unit on electrical connection of the second unit to the first unit. In another embodiment, selection of which power source is utilised can be controlled by the implantee, a clinician or another person.

In yet a further event of this aspect, the second unit has a switch means that activates and deactivates componentry of the second unit.

In a still further embodiment, the first unit can be useable with an implantable unit. Such an implantable unit can be adapted to work when necessary, in conjunction with the first unit. The implantable unit can though be adapted to work in a stand-alone mode.

The implantable unit can comprise:
(i) a hermetically sealed housing comprising:
  (a) an implantable power source that provides the power requirements of the implantable unit when operating in a stand-alone mode;
  (b) an implantable microphone that detects sounds and outputs acoustic data signals representative of said detected sounds; and
  (c) an implantable speech processor means that receives the acoustic data signals of the implantable microphone and converts the signals into stimulation signals representative of the detected sounds;
(ii) an electrode array suitable for insertion in the cochlea of an implantee, the array once inserted being adapted to receive the stimulation signals from the implantable speech processor and output electrical stimulation to the implantee's auditory nerve; and
(iii) an antenna coil suitable for implantation in the implantee.

In this embodiment, an external antenna coil is inductively couplable with the antenna coil of the implantable unit to provide a radio frequency (RF) link between the implantable cochlear stimulator and the fist unit. This radio frequency link allows a coded signal output by the first speech processor housed within the first unit, and/or the second speech processor housed within the second unit, to be transmitted to the electrode array of the implantable unit. This may be desirable, for example, in instances where one or more components of the implantable unit are inoperable for any reason.

According to a still further aspect, the present application is directed to another invention comprising an accessory for use with a cochlear implant system, the system having an external component including a microphone that detects sounds and outputs acoustic data signals representative of the detected sounds, and a speech processor means that receives the acoustic data signals;
  the accessory comprising:
  a power source and power transmission means adapted to provide power to at least the external component of the cochlear implant system; and
  a second microphone that detects sounds and outputs acoustic data signals representative of the detected sounds to the speech processor means of the system.

The second microphone of this and the other aspects provided herein can be identical to the microphone used in the external component or first unit of the cochlear implant system. Where used, the second microphone can be used to provide binaural hearing for the implantee. The second microphone can be an electret-type microphone. In another embodiment, the second microphone can utilise a piezoelectric polymer or piezo-ceramic material.

The second microphone can comprise a hearing aid microphone as known in the art. An example of a suitable microphone is a Knowles microphone.

In the aspects, an electrically conducting lead can be used as a means of transmitting the acoustic data signals output from the second microphone of each of the aspects to the external component or first unit of the cochlear implant system. In another embodiment, the acoustic data signal can be transmitted by a wireless means. In one embodiment, the acoustic data signal can be transmitted by a relatively short-distance radio frequency (RF) link.

In this aspect, the accessory can further comprises a receiver unit that is adapted to detect signals from an external source, when present, and output acoustic data signals representative of the detected sounds to the speech processor means of the system.

In the aspects provided herein, the receiver unit can comprise a telecoil. Telecoils are used by hearing impaired listeners in particular situations which usually involve group situations in organised venues, such as classrooms, meeting halls, conference rooms, music halls, cinemas and the like. Telecoils are designed to pick up magnetic fields generated by wire loops which enclose the area. Telecoils are also used to pick up magnetic signals from a telephone to avoid acoustic interference in noisy situations.

In the aspects, the receiver unit can be adapted to receive frequency modulated (FM) and/or amplitude modulated (AM) signals. The receiver unit preferably includes a tuner means that allows an implantee or another person to tune the radio receiver to a desired FM or AM wavelength.

In the aspects, the power source of the accessory can comprise one or more batteries. The batteries can be rehargeable. The power source of the accessory preferably also provides power for the components of the accessory, such as the microphone. In another embodiment, the power source of the accessory can be used to provide a charging current to a rechargeable battery, if present being used as an on-board power source for the external component or first unit of the cochlear implant system.

As previously described, the power transmission means can comprise an electrical conduction means, such as electrically conducting wire or wires that is preferably provided between the power source of the accessory and the external component or first unit of the cochlear implant system. The electrical connection can be provided by an electrically conducting lead that extends from the accessory or second unit to the external component or first unit of the cochlear implant system. The electrically conducting lead can be removably connectable to the external component and/or the accessory. The respective ends of the lead are preferably each removably insertable within sockets within both the accessory or second unit and the external component or first unit.

According to yet a further aspect, the present application is directed to another invention comprising an accessory for use with a cochlear implant system, the implant having an external component including a microphone, and a speech processor means;
  the accessory comprising:
  a power source adapted to provide power to the external component of the cochlear implant system;
  a second microphone that detects sounds and outputs acoustic data signals representative of the detected sounds to the speech processor; and
  a receiver unit that detects signals from an external source, when present, and outputs acoustic data signals representative of the detected signals to the speech processor means of the system.

In a preferred embodiment of this aspect, the power source of the accessory, the microphone and the receiver unit of the accessory can have the features of the power source of the accessory, second microphone and receiver unit as defined above.

In this aspect, the cochlear implants system can have an on-board power source.

In this aspect, and where the first unit has an on-board power source, use of the power source of the accessory by the cochlear implant system can occur automatically on commencement of use of the accessory. For example, the cochlear implant system can be adapted to preferentially, and when available, draw power from the power source of the accessory on electrical connection of the accessory unit to the external component of the systems. In another embodiment, selection of which power source is utilised can be controlled by the implantee, a clinician or another person.

In this aspect, the accessory can comprise a case that can be worn on the body, for example in a pouch or pocket In a preferred embodiment, however, the case of the accessory is adapted to be worn behind the ear of the implantee that does not use the cochlear implant system. In another embodiment, the case of the accessory can be adapted to be worn within the ear canal of the ear of the implantee that does not use the cochlear implant system.

In a preferred embodiment, the accessory can include a switch means that activates and deactivates the accessory. The switch means can, for example, deactivate the accessory by disconnecting the power source from the circuitry for the other components of the accessory.

In another embodiment the accessory can include a switch means that allows the implantee or another person to control which component of the accessory is in operation. For example, as the accessory includes both a microphone and a receiver unit, the switch means can be adapted to only allow one or the other of these components to operate at any particular time.

In a preferred embodiment of this aspect the speech processor means of the implant receive the acoustic data signals and converts the into coded signals representative of the detected sounds.

In another embodiment of this aspect the accessory can further comprise a second speech processor means that receives the acoustic data signals of the second microphone and converts the data signals into coded signals representative of the detected sounds. These coded signals can then be transmitted by the signal transmission means to the external component of the implant instead of, or in addition to, the acoustic data signals of the second microphone. The second speech processor can also be used to provide the implantee with the option of using sound coding algorithms not supported by the on-board speech processor within the external component of the cochlear implant system.

According to a still further aspect, the present application is directed to a still further invention comprising an accessory for use with a cochlear implant system, the cochlear implant system comprising an external component and an implantable component;

the external component including
a microphone that detects sounds and outputs acoustic data signals representative of the detected sounds;
an on-board power source; and
an external antenna coil;
the implantable component including
a cochlear simulator; and
an implantable antenna coil inductively couplable with the external coil to provide a radio frequency link between the external and internal component;
the accessory comprising:
a speech processor means that receives and processes the acoustic data signals of the microphone and converts the signals into coded signals that are transmittable from the accessory to the external component through a signal transmission means and from the external component to the implantable cochlear stimulator through the radio frequency link.

In this aspect the signal transmission means preferably provides a means of transmission of the acoustic data signals of the microphone to the speech processor means.

In one embodiment, the signal transmission means can be a wireless means.

In a still further embodiment of this aspect, the accessory can have a power source. In this case, an electrical conduction means can extend between the external component and the accessory to allow transmission of power from the onboard power source of the external component to at least the speech processor means of the accessory.

In a further embodiment, the accessory can further comprise a second microphone that detects sounds and also outputs acoustic data signals representative of the detected sounds to the speech processor means within the accessory.

In this aspect the external component and/or accessory have a case, the respective cases of the external component and accessory each having an ear hook extending therefrom to allow the respective cases to be worn behind the respective ears of the implantee. The accessory can have a case adapted to be worn in an ear canal of an implantee. Still further, the external component can have a case adapted to be worn in an ear canal of an implantee. Yet further, the accessory and the external component each have a respective case adapted to worn in the respective ear canals of an implantee.

The accessory can further comprise a receiver unit that is adapted to detect signals from an external source, when present, and output acoustic data signals representative of the detected signals to the speech processor means. The receiver unit is preferably selected from the group comprising a telecoil and a radio receiver.

In all aspects, the cochlear implant system can include an implanted stimulator/receiver unit. The stimulator/receiver unit can include an electrode array adapted to be inserted into the cochlea.

The electrode array can be any type as is known in the art. It should be appreciated that the type of array used is not crucial to an understanding of the present invention and any type of array can be used with the system of the present invention provided that it is supported by the system.

The implant system can also include one or more extracochlear electrodes to support monopolar stimulation.

The accessory or second unit can incorporate a warning system that provides an indication to the implantee or another person that the battery or batteries of the power source within the accessory needs replacing or recharging. The warning system may generate a unique stimulus signal that the implantee is trained to recognise as an indication that the battery or batteries needs replacing or recharging.

In another embodiment, the accessory or second unit can incorporate an interrogation means that allows the implantee or another person to determine the charge level of the battery or batteries in the accessory or second unit.

The inventions described herein provide an alternative means that allows the overall dimensions of the external component of a cochlear implant system to either remain substantially the same or be further reduced compared to presently known external components while offering improved performance and/or additional capabilities. It also provides the possibility of allowing for the operation of the cochlear implant system to be shared between the external components allowing the external components to be smaller in dimension and less visible. The present invention also provides the option of allowing the external components to be customised to the requirements of the implantee, taking into consideration the implantee's needs and preferences.

In a preferred embodiment of all aspects, the implanted component of the cochlear implant system includes a wire antenna coil. The antenna coil is preferably comprised of at least two, turns of electrically insulated wire tuned to parallel resonance by a capacitor. The electrical insulation of the antenna coil can be provided by a flexible silicone moulding and/or silicone or polyurethane tubing. The antenna coil is disposed about a centrally located magnet. The magnet can comprise a rare earth permanent magnet hermetically sealed within a titanium case. The magnet within its case is preferably held in the centre of the antenna coil by the silicone moulding surrounding the antenna coil. In a preferred embodiment the magnet is removable from the system so as to allow the implantee to undergo magnetic resonance imaging (MRI) scanning. Electrical connection between the coil and the other componentry of the implanted component can be provided by two hermetic and insulated ceramic feedthroughs or an electrical connector. The ceramic feedthrough can be formed using the method described in abovementioned U.S. Pat. No. 5,046,242. The coil can act as a radio frequency (RF) link to allow bidirectional data transfer between the implanted component of the system and the external component.

The speech processor means of the cochlear implant system preferably performs an audio spectral analysis of the acoustic data signals and outputs channel amplitude levels. The speech processor means can also sort the outputs in order of magnitude or flag the spectral maximum as used in the SPEAK strategy developed by Cochlear Ltd.

The implanted component can include at least a stimulation processor that performs a stimulation strategy process, stimulus level mapping and output control. The input to the stimulation processor comes from the speech processor means, whether it be an implanted speech processor means or a speech processor means housed in an external component as defined herein. The role of the stimulation processor is well known in the art and has been performed in all conventional cochlear implant systems to deliver the stimulus to the intra-cochlea arrays. As such it is considered that a person skilled in the art would understand and appreciate the function performed by the stimulation processor in the current invention.

In another embodiment, the accessory or second unit as described above car include an external controller for the accessory, second unit and/or the cochlear implant system. Such a controller can provide a remote means of diagnosing and adjusting implant system parameters and also provide a means of selecting different speech processing strategies. For example, the controller can allow the implanted or a clinician to diagnose and adjust the sensitivity of the one or more speech processor means and/or the level of stimulation output by the electrode array.

The external controller also preferably provides the clinician or implantee with a means of interrogating the cochlear implant system to determine the status of the on-board power source, such as the level of charge of the battery, as well as other useful system information. The external controller also provides the clinician or implantee with a means of measuring the performance of the processor means and/or the microphone of the cochlear implant system. The external controller can communicate with the cochlear implant system through an electrical lead or wireless radio frequency (RF) link between the accessory or second unit and the cochlear implant system.

BRIEF DESCRIPTION OF THE DRAWINGS

By way of example only, embodiments of the present inventions are now described with reference to the accompanying drawings, in which.

PREFERRED MODE OF CARRYING OUT THE INVENTION

Figure 1:
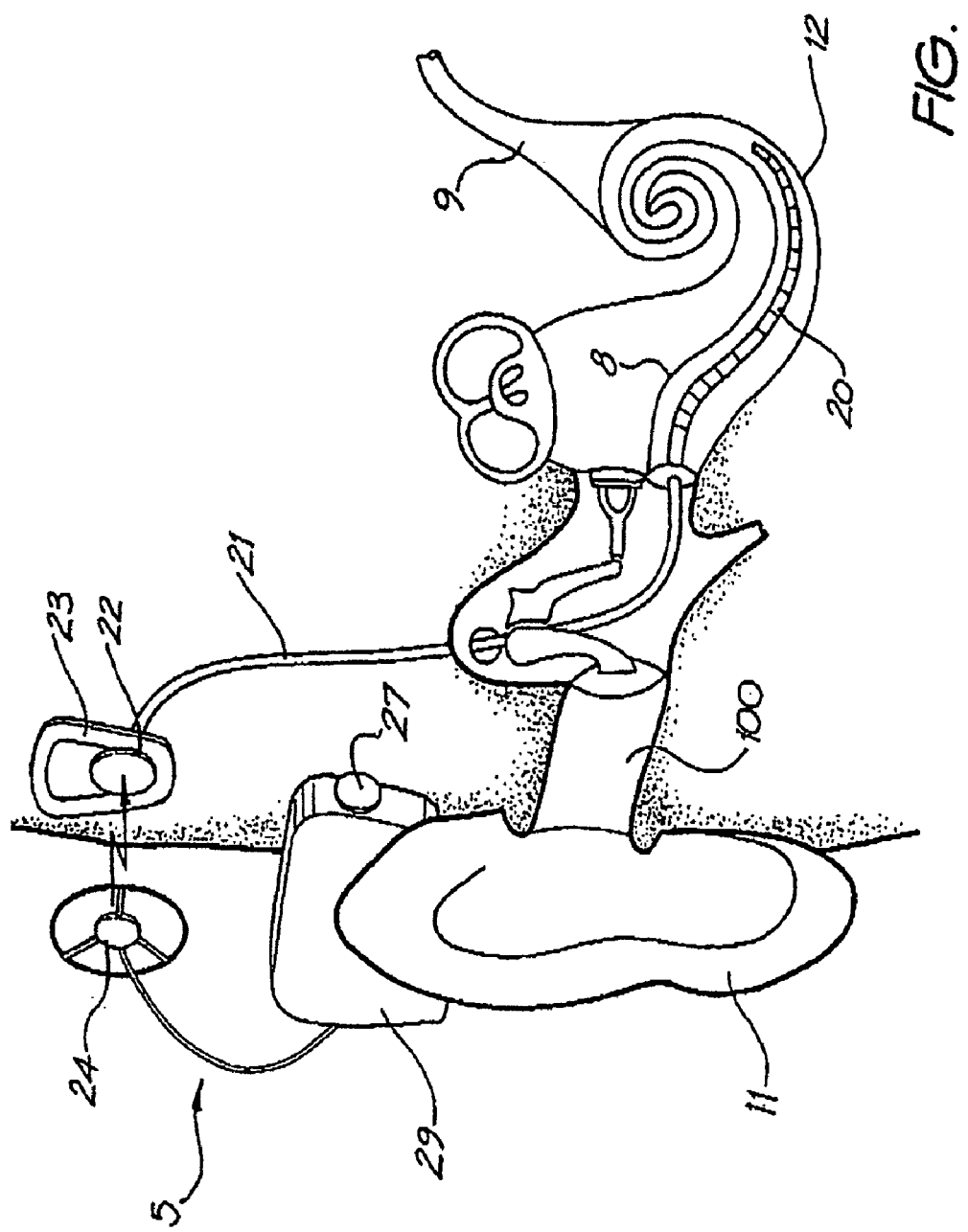
FIG. 1 is a pictorial representation of a prior art cochlear implant system.

Before describing the features of the present invention, it is appropriate to briefly describe the construction of one type of known cochlear implant system with reference to FIG. 1.

One type of known cochlear implant system 5 typically consists of two main components, an external component including a speech processor 29, and an internal component including an implanted receiver and stimulator unit 22. The external component includes an onboard microphone 27. The speech processor 29 is, in this illustration, constructed and arranged so that it can fit behind the outer ear 11. Alternative version may be worn on the body or within the ear canal 100. Attached to the speech processor 29 is a transmitter coil 24 which transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. The operation of such a device is described, for example, in U.S. Pat. No. 4,532,930.

The speech processor 29 of the cochlear implant system 5 can perform an audio spectral analysis of the acoustic data signals from the microphone 27 and outputs channel amplitude levels. The speech processor 29 can also sort the outputs in order of magnitude or flag the spectral maxima as used in the SPEAK strategy developed by Cochlear Ltd.

Figure 2:
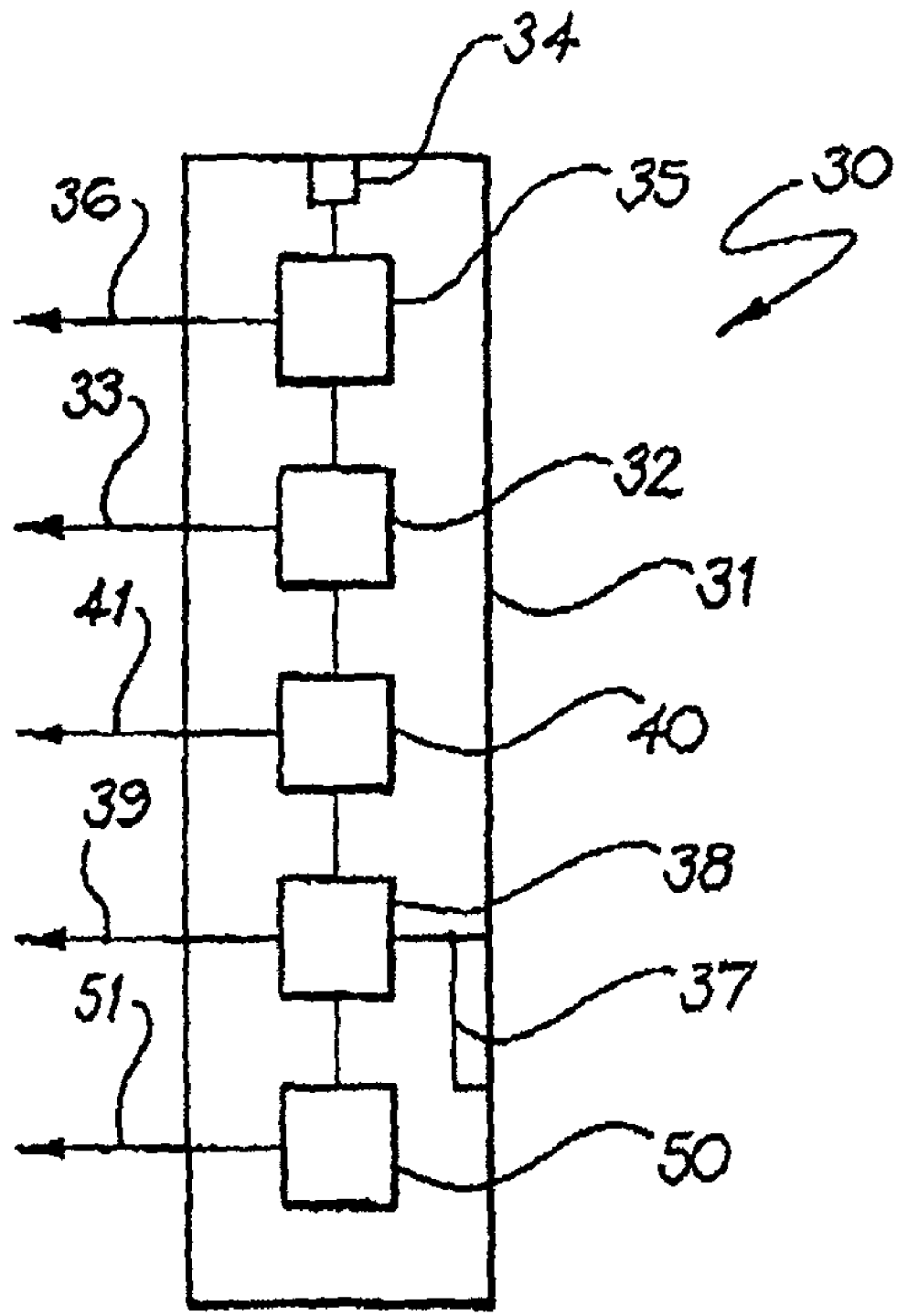
FIG. 2 is a schematic view of one embodiment of an accessory for a cochlear implant system according to the present invention.

One embodiment of an accessory for a cochlear implant system 5 according to the present invention is depicted schematically as 30 in FIG. 2. In this embodiment, the accessory 30 is adapted to be worn behind and supported by the ear of an implantee that is not implanted with the cochlear implant system 5. It will be appreciated that the accessory could also be supported in a pouch or pocket carried or worn by the implantee or adapted to be worn within the ear canal of the ear of the implantee that is not implanted with the cochlear implant system 5. The accessory 30 can be used in conjunction with the dedicated cochlear implant processor 29 as depicted in FIG. 1. The accessory 30 can, however, be used in conjunction with a totally implantable cochlear implant system having an implanted speech processor and microphone that is adapted to operate, at least for a certain period, in a stand-alone mode or an implant that is positioned within the ear canal 100 of the implantee. Still further, the accessory 30 can be adapted to be used with a speech processor 29 that is housed in a case that is adapted to be worn in the ear canal 100 of the implantee.

The accessory 30 has an external case 31 enclosing an additional power source 32. The power source 32 comprises one or more battery cells. The cells in the depicted embodiment are rechargeable.

The power source 32 can be used to provide power to the speech processor 29 and other componentry of the cochlear implant system 5 through electrical connection 33. The power provided by power source 32 can be used by the cochlear implant system 5 either in combination with or instead of any on-board power source within or electrically connected to the cochlear implant processor 29. The additional power source 32 can also be used to provide a charging current to a rechargeable battery being used as the on-board power source for the cochlear implant system 5. In another arrangement, the accessory 30 can be used with a cochlear implant system that does not have its own on-board power source. In this case, power for the cochlear implant system and the accessory 30 is provided by power source 32.

As depicted in FIG. 2, the accessory 30 can also include an additional microphone 34 and microphone signal amplifier 35. The microphone 34 detects sounds and outputs acoustic data signals representative of the detected sounds through the amplifier 35 to the speech processor 29 through signal connection 36.

In one embodiment, the additional microphone 34 be identical to the microphone 27 used with the dedicated cochlear implant processor 29. When used, the additional microphone 34 provides binaural hearing for the implantee. The depicted additional microphone 34 is an electret-type microphone. In another embodiment the additional microphone can utilise a piezoelectric polymer or piezo-ceramic material.

In the depicted embodiment, it is envisaged that signal connection 36 is provided by a cable extending between the case 31 of the accessory 30 and the cochlear implant processor 29. In another embodiment the means of transmitting the acoustic data signals output from the additional microphone 34 to the cochlear implant processor 29 can comprise a wireless means. For example, the acoustic data signals could be transmitted by a relatively short-distance radio frequency (RF) link.

The depicted accessory 30 further includes an antenna 37 and radio receiver 38. The antenna 37 and receiver 38 detect radio frequency (RF) signals and output acoustic data signals representative of the detected radio frequency signals through signal connection 39 to the speech processor 29 of the cochlear implant system 5.

The accessory 30 can further comprise a telecoil system 40. Telecoils are used by implantees in situations such as classrooms, meeting halls, conference roams, music halls and the like and pick up magnetic fields generated by wire loops which enclose the area. Telecoils are also used to pick up magnetic signals from a telephone to avoid acoustic interference in noisy situations. The telecoil 40 detects such signals and outputs signals representative of the detected signals to the speech processor 29 via signal connection 41.

The receiver 38 can be tuned or switched to receive radio frequency signals of different frequencies. The receiver 38 can also be switched or tuned to receive frequency modulated (FM) and/or amplitude modulated (AM) signals. The radio receiver preferably includes a tuner means that allows an implantee to tune the radio receiver to a desired FM or AM wavelength.

The additional power source 32 is also used in the accessory 30 to provide power for the components of the accessory, including the microphone 34, amplifier 35, receiver 38 and telecoil 40.

The accessory 30 can be provided with a switch that activates and deactivates the accessory 30. The switch can deactivate the accessory 30 by disconnecting the power source 32 from the circuitry for the other components, such as the amplifier 35, receiver 38 and telecoil 40.

The accessory 30 can also include a switch that allows the implantee to control which component of the accessory 30 is in operation. For example, where the accessory includes both the microphone 34 and the radio frequency receiver 38, the switch can be adapted to only allow one or the other of these components to operate at any particular time.

The accessory 30 can also incorporate a warning system that provides an indication to the implantee that the battery or batteries of the additional power source 32 needs replacing or recharging. The warning system may lead to the generation of an unique stimulus signal that the implantee is trained to recognise as an indication that the battery or batteries needs replacing or recharging.

In another embodiment, the accessory 30 can incorporate an interrogation means that allows the implantee to determine the charge level of the battery or batteries in the accessory 30.

In another embodiment, the accessory 30 can include an external controller for the accessory 30 and/or the dedicated cochlear implant processor 29. Such a controller can provide a remote means of diagnosing and adjusting implant or accessory parameters and also provide a means of selecting different speech processing strategies. For example, the controller can allow the implantee or a clinician to diagnose and adjust the sensitivity of the speech processor 29 and/or the level of stimulation output by the electrode array 20.

The external controller also preferably provides the clinician or implantee with a means of interrogating the cochlear implant system 5 or accessory 30 to determine the status of the on-board power source, such as the level of charge of the battery, as well as other useful system information. The external controller also provides the clinician or implantee with a means of measuring the performance of the speech processor 29 and/or the microphone 27 of the cochlear implant processor 29. The external controller can communicate with the cochlear implant system 5 through an electrical lead or wireless RF link between the accessory 30 and the cochlear implant processor 29.

In another embodiment, and as depicted, the accessory 30 can include an on-board speech processor 50. The onboard speech processor 50 can also be used to provide the implantee with the option of using sound coding algorithms not supported by the speech processor 29 within the cochlear implant system 5. In the depicted embodiment, it is envisaged that a signal connection 51 between the speech processor 50 and the cochlear implant processor 29 is provided by a cable extending between the case 31 of the accessory 30 and the cochlear implant processor 29. In another embodiment, the means of transmitting the acoustic data signals output from the speech processor 50 to the cochlear implant processor 29 can comprise a wireless means. For example, the signals could be transmitted by a relatively short-distance radio frequency (RF) link.

It is envisaged that the accessory 30 of the present invention can incorporate any one or a number of elements 32, 34, 35, 37, 38, 40 and 50 as depicted in FIG. 2, and remain within the scope of the present invention. For example, the accessory 30 may only comprise the speech processor 50. In this case, the speech processor 50 my receive acoustic data signals from the microphone 27, and/or a microphone 34 positioned on the accessory 30, and/or a microphone in another location In this case, the cochlear implant system being used in conjunction with the accessory 30 may or may not have an on-board speech processor.

In the depicted embodiment, the electrical connections 33, 38, 39, 41 and 51 can be provided through a single cable that extends between the case of the speech processor 29 and the case 31 of the accessory 30. When the accessory 30 and speech processor 29 are being worn on the respective ears of the implantee, the cable can extend around the back of the head of the implantee.

Figure 3:
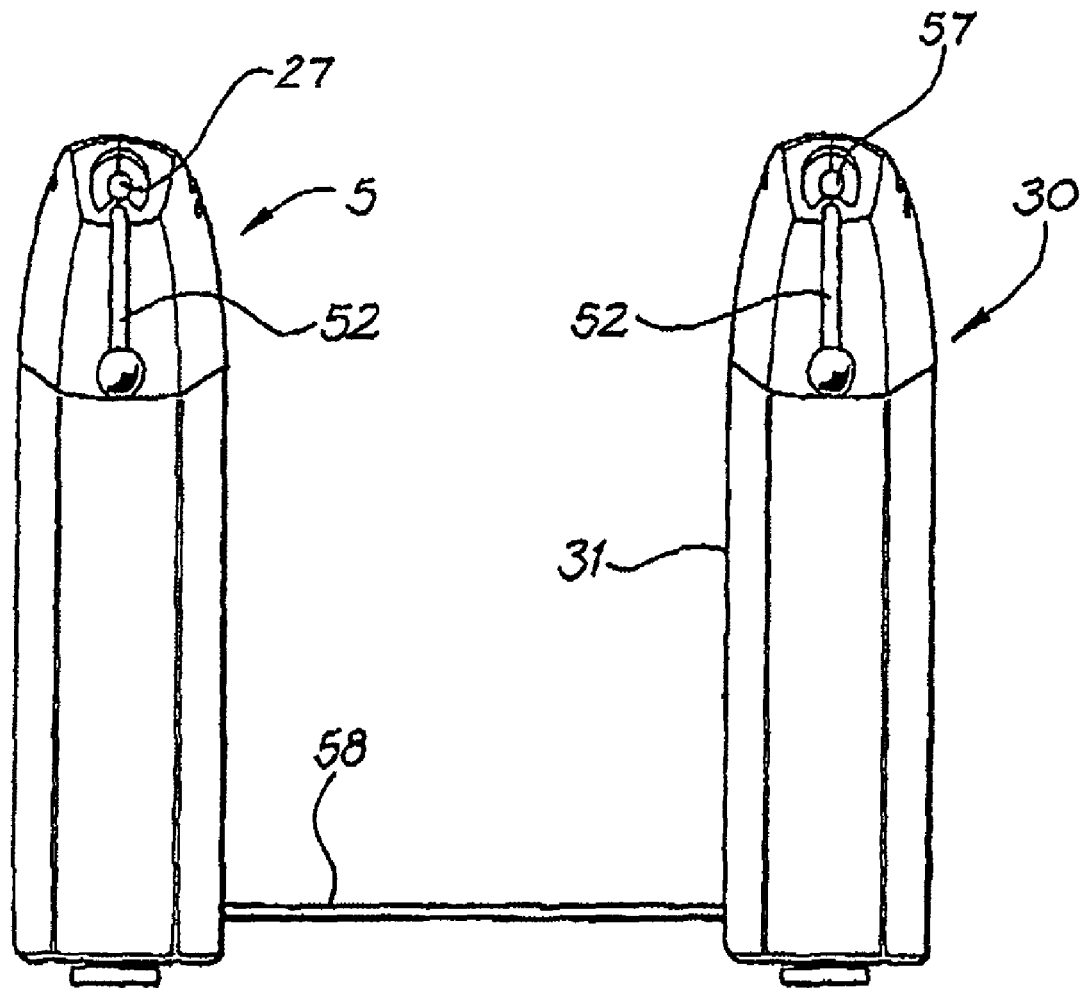
FIG. 3 is a pictorial representation of a cochlear implant system according to the present invention.

FIG. 3 depicts one example of an accessory 30 being used in conjunction with the external component of a cochlear implant system 5. In this embodiment, both the external component of the cochlear implant system 5 and the accessory 30 have an ear hook 52. As depicted, the external component of the cochlear implant system is adapted to be hooked to the right ear of the implantee and the accessory 30 is adapted to be hooked to the left ear of the implantee. It will, however, be appreciated that the respective locations of the cochlear implant processor 29 and accessory 30 could be readily swapped if in fact the implantee normally used the implant 5 with their left ear. While the respective cases of the cochlear implant processor 29 and the accessory 30 are depicted as having the same shape, it will be appreciated that the cases could be different shapes. The cochlear implant system 5 could also be different to that depicted, for example, the implant could be adapted to be worn in the ear canal of the implantee. Still further, the implant could be totally implantable cochlear implant system. Still further, the case of the accessory 30 could also be dimensioned and shaped to fit with the ear canal of the implantee.

In the embodiment depicted in FIG. 3, the cochlear implant system 5 has an on-board power source, a speech processor and a microphone 27. The accessory 30 also has a microphone 57, which in the depicted embodiment is identical to the microphone 27 mounted in the cochlear implant processor 29. Housed within the case 31 of the accessory 30 is a further power source. When the accessory 30 is used in conjunction with the cochlear implant system 5, the power source in the accessory can be used to provide power to componentry of the accessory 30 and the cochlear implant system 5. The transmission of power from the accessory 30 to the cochlear implant system 5 is provided by wiring housed within cable 58. Cable 58 is, in the depicted embodiment, removably connectable to the rear face of the respective components. The cable 58 can stretch to comfortably extend between the cochlear implant processor 29 and the accessory 30 when the respective components are mounted to the respective ears of the implantee. In normal use, it is envisaged that the cable 58 would extend around the back of the head of the implantee between the two ears.

It will be appreciated that the case 31 could house a speech processor or other componentry as has been described herein. Signal connection from the accessory 30 to the cochlear implant system 5 for this componentry can also be provided by appropriate wiring housed within cable 58. As already described, the speech processor in the accessory 30 cam be used instead of or in conjunction with the speech processor housed in the cochlear implant system 5.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An accessory for a cochlear implant system comprising an external component having a first speech processor, wherein the external component is configured to be worn on or in the ear canal of an implantee's first ear, the accessory comprising:
    a case configured to be worn on or in the ear canal of the implantee's second ear; and
    an accessory element disposed in the case and configured to provide one or more of power and data to the external component via a transmission system, wherein the accessory element is one of a power source, a microphone, a second speech processor, a radio receiver, and a telecoil system.

2. The accessory of claim 1, wherein accessory element is the power source and the transmission system is configured to provide power from the power source to the external component.

3. The accessory of claim 2, wherein the accessory further comprises:
    the second speech processor; and
    the microphone, wherein the microphone is configured to detect sounds and to provide acoustic data signals representative of the detected sounds to the second speech processor, the second speech processor is configured to generate coded data signals based on the acoustic data signals, and the transmission system is configured to provide the coded date signals from the accessory to the external component.

4. The accessory of claim 3, wherein the transmission system comprises first and second electrical leads and a cable housing the first and second electrical leads, and wherein the first electrical lead is configured to provide power from the power source to the external component and the second electrical lead is configured to provide the coded data signals from the second speech processor to the external component.

5. The accessory of claim 1, wherein the transmission system comprises a wireless transmission system, and wherein the wireless transmission system is configured to provide power from the power source to the external component.

6. The accessory of claim 1, wherein the accessory further comprises:
    the radio receiver, wherein the radio receiver is configured to detect radio frequency (RF) signals and output data signals based on the detected signals, and wherein the transmission system is configured to provide the data signals from the accessory to the external component.

7. The accessory of claim 1, wherein the accessory further comprises:
    the telecoil, wherein the telecoil is configured to detect one or more of magnetic signals and signals transmitted via a magnetic field and output data signals based on the detected signals, and wherein the transmission system is configured to provide the data signals from the accessory to the external component.

8. A cochlear implant system comprising:
    a first unit, configured to be worn on or in the ear canal of an implantee's first ear, and comprising a first speech processor;
    a second unit configured to be worn on or in an ear canal of the implantee's second ear; and
    a transmission system configured to transmit one or more of power and data between the first and second units.

9. The cochlear implant system of claim 8, wherein the second unit comprises:
    a power source, wherein the transmission system is configured to transmit power from the power source to the first unit.

10. The cochlear implant system of claim 9, wherein the second unit further comprises:
    a microphone; and
    a second speech processor, wherein the microphone is configured to detect sounds and provide acoustic data signals representative of the detected sounds to the second speech processor, the second speech processor is configured to generate coded data signals based on the acoustic data signals, and the transmission system is configured to provide the coded data signals from the second unit to the first unit.

11. The cochlear implant system of claim 10, wherein the transmission system comprises:
   a first electrical lead configured to transmit power from the power source to the first unit;
   a second electrical lead configured to transmit the coded data signals from the second speech processor to the first unit; and
   a cable housing the first and second electrical leads.

12. The cochlear implant system of claim 8, wherein the transmission system comprises:
   a wireless transmission system.

13. The cochlear implant system of claim 12, wherein the wireless transmission system comprises:
   a radio frequency (RF) link between the first and second units.

14. The cochlear implant system of claim 8, wherein the second unit comprises:
   an antenna; and
   a radio receiver electrically connected to the antenna, wherein the antenna and radio receiver are configured to detect radio frequency (RF) signals, the radio receiver is configured to generate data signals representative of the detected RF signals, and the transmission system is configured to provide the data signals from the second unit to the first unit.

15. The cochlear implant system of claim 8, wherein the second unit comprises:
   a telecoil system configured to detect one or more of magnetic signals and signals transmitted via a magnetic field, and to generate data signals representative of the detected signals, wherein the transmission system is configured to provide the data signals from the second unit to the first unit.

16. A method of operating a cochlear implant system, the cochlear implant system comprising a first unit having a speech processor, a second unit, a transmission system, and an implanted component, wherein the first unit is configured to be worn on or in the ear canal of an implantee's first ear and the second unit is configured to be worn on or in the ear canal of the implantee's second ear, the method comprising:
   transmitting, via the transmission system, one or more of power and data between the first and second units; and
   transmitting one or more of power and data from the first unit to the implanted component.

17. The method of claim 16, wherein the second unit comprises a power source, and wherein transmitting, via the transmission system, one or more of power and data between the first and second units comprises:
   transmitting power, via the transmission system, from the power source to the first unit.

18. The method of claim 17, wherein the second unit further comprises a microphone and a second speech processor, wherein the method further comprises:
   detecting sounds via the microphone;
   providing acoustic data signals representative of the detected sounds to the second speech processor; and
   providing coded data signals based on the acoustic data signals to the first unit via the transmission system.

19. The method of claim 18, wherein the transmission system comprises, first and second electrical leads and a cable housing the electrical leads, and wherein transmitting, via the transmission system, one or more of power and data between the first and second units comprises:
   transmitting power, via the first electrical lead, from the power source to the first unit; and
   transmitting the coded data signals, via the second electrical lead, from the second speech processor to the first unit.

20. The method of claim 16, wherein the transmission system comprises a wireless transmission system, and wherein transmitting, via the transmission system, one or more of power and data between the first and second units comprises:
   wirelessly transmitting, via the transmission system, one or more of power and data between the first and second units.

21. The method of claim 16, wherein the second unit comprises a radio receiver, and wherein transmitting, via the transmission system, one or more of power and data between the first and second units comprises:
   providing data signals, via the transmission system, from the radio receiver to the second unit.

22. The method of claim 16, wherein the second unit comprises a telecoil, and wherein transmitting, via the transmission system, one or more of power and data between the first and second units comprises:
   providing data signals, via the transmission system, from the telecoil to the second unit.

* * * * *